United States Patent [19]

Mathur et al.

[11] Patent Number: 5,234,915
[45] Date of Patent: Aug. 10, 1993

[54] BIODEGRADABLE GEL

[75] Inventors: Rajiv Mathur, Nashua; Donald F. H. Wallach, Hollis, both of N.H.

[73] Assignee: Micro Vesicular Systems, Inc., Nashua, N.H.

[21] Appl. No.: 587,240

[22] Filed: Sep. 24, 1990

Related U.S. Application Data

[63] Continuation-in-part of Ser. No. 320,944, Mar. 9, 1989, Pat. No. 4,959,341.

[51] Int. Cl.$^5$ .................. C08H 1/00; C07K 13/00; A61K 31/545; A61K 47/00
[52] U.S. Cl. ................... 514/57; 514/449; 514/460; 514/777; 524/27; 521/139; 546/290; 604/368
[58] Field of Search ............ 514/57, 23, 11, 200, 514/777, 449, 460, 252, 312; 536/27; 524/21; 546/290; 521/139; 604/368; 252/194; 424/426, 85.8, 426; 527/312

[56] References Cited

U.S. PATENT DOCUMENTS

| | | | |
|---|---|---|---|
| 3,969,280 | 7/1976 | Sayce et al. | 252/522 |
| 4,090,013 | 5/1978 | Ganslaw et al. | 526/15 |
| 4,160,063 | 7/1979 | Titus | 428/389 |
| 4,486,335 | 12/1984 | Majewicz | 252/315.3 |
| 4,610,678 | 9/1986 | Weisman et al. | 604/368 |
| 4,616,008 | 10/1986 | Hirai et al. | 514/777 |
| 4,786,415 | 11/1988 | Shibata et al. | 210/635 |
| 4,812,486 | 3/1989 | Hosokawa et al. | 521/139 |
| 4,826,880 | 5/1989 | Lesniak et al. | 521/53 |
| 4,871,741 | 10/1989 | Gadebusch et al. | 514/460 |
| 4,874,850 | 10/1989 | Paradies | 546/290 |
| 4,988,697 | 1/1991 | Onishi | 514/449 |
| 5,015,677 | 5/1991 | Benedict et al. | 524/21 |

FOREIGN PATENT DOCUMENTS

| | | |
|---|---|---|
| 1152483 | 8/1983 | Canada . |
| 745504 | 2/1974 | France .................. 514/57 |
| 212969 | 8/1984 | German Democratic Rep. . |
| 60-021953 | 2/1985 | Japan . |
| 62-112654 | 5/1987 | Japan . |

OTHER PUBLICATIONS

Popovici et al.; Abstract; Chemical Abstracts, vol. 86 (20); pp. 145841.

*Primary Examiner*—Michael G. Wityshyn
*Assistant Examiner*—L. N. Leary

[57] ABSTRACT

A new gel-like composition of matter containing a complex carbohydrate with a high degree of carboxyl substitution cross-linked by an organic cross-linker has been developed. The cross-linkers have complex ring structures, e.g., polynuclear or heterocyclic compounds, which permit development of two distinct partial positive charges under conditions where a carbohydrate is negatively charged. Antibiotics are the preferred cross-linking agents and a method of sustained release of the antibodies is also disclosed.

11 Claims, No Drawings

BIODEGRADABLE GEL

REFERENCE TO RELATED APPLICATIONS

This application is a continuation-in-part of U.S. Pat. Application Ser. No. 320,944, filed Mar. 9, 1989, now U.S. Pat. No. 4,959,341, entitled "Biodegradable Superabsorbing Sponge," the disclosure of which is incorporated herein.

BACKGROUND OF THE INVENTION

The present invention relates to biodegradable gels which act as superabsorbing sponges and hydrogels. More particularly, the gel of the invention can have as high, or higher, liquid and saline uptake than the polyacrylate superabsorbers now being used while having the advantage of being completely biodegradable. Further, if used as a hydrogel, the gel has superior properties than current hydrogels while being completely biodegradable into organic compounds.

Biodegradability has become a necessity in society in the last few years. As more and more products are made disposable, the waste problems associated with these disposables have become increasingly important. One example of this is the disposable diaper field. Until a few years ago, disposable diapers, though convenient, had not received widespread use because the amount of liquid which could be absorbed was limited. This limitation lead to use of the diapers for extraordinary circumstances but they were not feasible for most people on a day-to-day basis because of the leakage and resulting diaper rash problem. In order to solve these problems, the diaper manufacturers first used very thick diapers, placing large amounts of fiber such as cellulose in the diaper to act as a liquid, primarily saline and urine, absorber. These bulky diapers still had limitations on the amount of liquids they could retain while the bulk made them uncomfortable for the infants to wear.

The first major improvement in the disposable diaper field was the addition of the so-called "superabsorbers" as liquid traps. These superabsorbers are primarily polyacrylate particles which are placed in the diaper in loose form or are entrapped among cellulose fibers. These polyacrylate particles absorb large quantities of water by swelling and acting as individual pseudo-sponges. Since the amount of saline and urine which can be absorbed by these superabsorbers is so much greater than cellulose or other natural fibers, very thin diapers could be used, minimizing the problems to infants and making disposables the diaper of choice.

In addition to the use in diapers, the superabsorbers have other uses. Many other items which are used for absorption of liquid are a fertile ground for use of the superabsorbers. However, the polyacrylate superabsorbers have one major disadvantage; they are not biodegradable. This means that the diapers and all other products made using these superabsorbers are not dissociated for decades; in fact, they need hundreds of years to breakdown. This leads to the aforementioned waste problem. Another disadvantage of the polyacrylates is that they absorb maximally at 0% saline while urine and most body fluids are about 0.9% saline.

Materials which absorb liquid and are biodegradable such as the gels of the present invention may open other potential fields. The entrapment of particles, including macromolecules such as hemoglobin and cells such as erythrocytes, is particularly important for feminine napkins and similar products. Superabsorbers have not made a great dent in this field even though they have the necessary liquid absorption because they cannot entrap large particulates.

Another possible use for a biodegradable gel which will entrap liquid and/or particles is as a sustained release vehicle. In certain instances, the molecules to be delivered can be part of the structural material of the sponge itself. Most materials which are presently being tested as sustained release vehicles, e.g., microcapsules, liposomes and related capsular type products, have substantial costs and time associated with their manufacture. The ability to make a product in situ. apply it to a given area, and then let it dissociate under ordinary conditions to release entrapped material, would solve many problems.

A further use of a gel which entraps liquids and particles is as a biological protective barrier. For example, a gel which entraps bacteria as it is hydrated, or prevents their passage once formed, can be used as a wound dressing, protecting the wound from bacteria while allowing free flow of liquid to the injury. A further use is in a diaper where coliform bacteria can break down urea in urine to ammonia, changing the pH and promoting diaper rash.

Hydrogels are also found in a variety of products because of their thickening action. For example, many shampoos use hydrogels to provide "body," giving consumers the impression that they obtain enhanced cleaning action from the thickened shampoos.

Accordingly, an object of the invention is to provide an organic, biodegradable gel that has high uptake for water and saline.

Another object of the invention is to provide a biodegradable carrier or sustained release delivery system for drugs and other molecules.

A further object of the invention is to provide a material and method for entrapment of particulates such as erythrocytes and protein molecules such as hemoglobin.

A still further object of the invention is to provide a protective barrier which prevents the passage of particles such as bacteria or macromolecules, e.g., for use as a wound bandage.

An additional object of the invention is to provide a method of delivering an antibiotic to a particular location which is released over time as the material dissociates.

A still further object of the invention is to provide an inexpensive, biodegradable hydrogel.

These and other objects and features of the invention will be apparent from the following description.

SUMMARY OF THE INVENTION

The present invention features a composition of matter in the form of a gel which acts as a synthetic sponge or a hydrogel and is biodegradable. The gel has an organic cross-linking agent which provides both cross-linking and a degree of hydrophobicity needed to support the gel structure. The invention further features a method of sustained release for antibiotics where the antibiotics themselves are used as a cross-linking agent in the gel.

More particularly, a composition of matter has been developed which contains a complex carbohydrate with a high degree of carboxyl substitution, preferable a degree of substitution (DS) of 0.5 or greater. This complex carbohydrate is cross-linked by an organic cross-linking agent selected from the group consisting of substituted polynuclear compounds and substituted heterocyclic compounds, with the cross-linking agent having at least two distinct partial positive charge locations under conditions, e.g., ionic strength and pH, when the complex carbohydrate has a localized negative charge. As used herein, the term "substituted polynuclear compounds" means compounds having at least two attached aromatic ring structures with side groups on at least one of the ring structures, e.g., by electrophilic substitution or addition reactions. The term "substituted heterocyclic compounds" means compounds with ring structures also having at least one non-carbon atom in the ring, the ring structure having a side group inserted by substitution or addition. These compounds are further described in standard organic textbooks, e.g., see Morrison and Boyd, "Organic Chemistry" (Allyn and Bacon, Inc.). The complex carbohydrates with a sufficiently high DS will have localized negative charges across a large pH range except very acidic pH. The cross-linking agents useful in the present invention have structures such that partial positive charges can be obtained at least two distinct locations on the molecule, so that the molecule can act as an ionic cross-linking agent between two carbohydrates. The composition may also include a linear carbohydrate such as a cellulose.

Preferred polynuclear compounds useful in the invention are tetracyclines and quinones. The tetracyclines, particularly tetracycline itself, oxytetracycline and dozytetracycline, all have the following ring structure

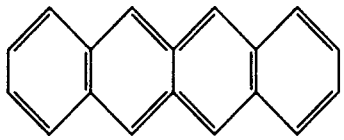

Similarly, the quinones primarily useful in the invention have a dual ring structure with two bonded oxygens as shown in the following illustration.

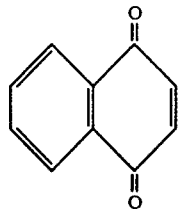

While there are a variety of heterocyclic ring structures which could be used in the present invention, those which include a nitrogen bearing ring are preferred. The nitrogen bearing ring structures having sufficient resonance include imidazoles, purines, pyrimidines, and quinolines. The preferred imidazoles have the structure

where R is selected from the group consisting of substituted aromatic ring molecules, polynuclear compounds, and heterocyclic compounds with a alkane or alkene side chains. More preferred imidazoles are conazoles such as econazole or miconazole.

Many of the heterocyclic and polynuclear compounds useful in the invention show antibiotic activity. Accordingly, a further aspect of the invention is a method of delivering antibiotics in a sustained release manner. Briefly, the method has the steps of forming the gel composition as previously described using an antibiotic as a cross-linking agent, delivering the composition to a body at a location where the sustained release is sought, and allowing the composition to dissociate, whereby the antibiotic is released in a sustained manner. Preferred antibiotics for use in this method include quinolines such as norfloxacin, tetracyclines such as oxytetracycline and a variety of conazoles. The antibiotic delivery system could be used in animals or humans through surface patches, wound dressings, or in an injectable form.

Other features of the invention will be apparent from the following detailed description and the claims.

DETAILED DESCRIPTION OF THE INVENTION

The present invention provides a gel-like composition which may be used as a superabsorber, a hydrogel, a sustained release vehicle, an entrapment molecule, and for a variety of other uses. The gels formed are stable so long as they are moist and pH range is not varied such that the ionic cross-linking is interrupted. Normally, the gels are stable in a slightly acidic to neutral pH while at very high acid or alkaline pH, the gels disintegrate.

A variety of factors can change the consistency and other properties of the gel to tailor the gel to desired specifications. For example, the use of an additional cross-linking agent such as the organo-metallic cross-linking agent described in U.S. Patent Applic. Ser. No. 320,944 can strengthen certain of the gels. As the concentration of the carbohydrate or the cross-linker rises, the stiffness and spreadability of the gels change, becoming stiffer as more carbohydrate or cross-linker is used. Changing the ionic strength of the fluid in the material also makes a difference in the property of the gels, with the gels tending to be more fluid at low ionic strengths and firmer at higher salt concentrations. This is in contrast to the carbopols often used in cosmetics as thickeners which collapse with increasing ionic strength. As noted, the gels are somewhat pH sensitive but appear substantially insensitive to pH changes between 3.5 and 6.5. Some or part of the water used in the gel may be replaced by other aqueous miscible solvents such as ethanol (up to 35%) or glycerol or propylene glycol (up to 60%).

The gels can encapsulate oils such as mineral oil, silicone oil, para-aminobenzoate esters, diethyltoluamide (DEET) and cinnamate sunscreens. The gels also may contain suspensions of a particulate such as benzoyl peroxide, or may contain a variety of water soluble amino acids, sugars, proteins, and water soluble dyes including dihydroxy acetone or amphotercin B. Further, the gels may contain a variety of other drugs such as erythromycin, salicylic acid, metronidazole, and retinoic acid. When the gels dry, they will form water vapor barriers on the skin which is of importance because of the skin moisturizer action.

The following non-limiting Examples will further illustrate the invention.

EXAMPLE 1

This Example shows a gel made using a tetracycline derivative, specifically oxytetracycline. Table 1 shows the ingredients and proportions used.

TABLE 1

| | |
|---|---|
| 5 mM Sodium Acetate in Water | 80 ml |
| Carboxymethylcellulose (CMC7L2P) | 2.12 g |
| Oxytetracycline HCl | 24 g |
| 2N Sodium Hydroxide | 21.4 ml |

The gel was made by dissolving the carboxymethylcellulose in the sodium acetate solution which had been heated to approximately 40° C. A clear solution is obtained. After cooling to 30–32° C., the oxytetracycline hydrochloride is added with stirring. The suspension is then mixed with sodium hydroxide and the pH is adjusted, using the sodium hydroxide, to 4.5. The gel sets instantly.

The resulting gel is a fine suspension which settles out of solution but can be redispersed. This gel, upon breakdown or dissociation, would yield the oxytetracycline, making it particularly useful for veterinary applications where oxytetracycline is used often as an antibiotic. A major benefit is that the oxytetracycline-carboxymethylcellulose complex is non-irritating.

EXAMPLE 2

In this Example, a quinone derivative, norfloxacin was used to make a gel. Norfloxacin (Sigma Chemical Company) has the formula

| |
|---|
| 1 Ethyl-6-fluro, 1, 4 dihydro 4 oxo-7 [1 piperazinyl]-3-quinoline carboxylic acid |

Norfloxacin is used as a veterinary antibiotic.

The ingredients shown in making the gel are listed in Table 2.

TABLE 2

| | | |
|---|---|---|
| A. | Carboxethylcellulose (CMC7L2P) | 4.0 g |
| | 0.9% Saline | 50 ml |
| B. | Norfloxacin | 6.0 g |
| | Acetic Acid | 2 ml |
| | 0.9% Saline | 50 ml |

The procedure used to make the norfloxacin gel was slightly different than that used to make the oxytetracycline complex. First 40 ml of 0.9% saline is heated to 40° C. and the carboxymethylcellulose is dissolved to give a clear solution. The solution is cooled to room temperature and 0.9% saline is added to make a volume of 50 ml. At the same time, the acetic acid is mixed with 40 ml of the 0.9% saline and the norfloxacin is dissolved into it. The volume is again corrected to 50 ml.

The two resulting solution are then mixed together, e.g., by mixing between two syringes. The resulting suspension, which can be sedimented by centrifugation and resuspended, is then adjusted to pH 4.5 using acetic acid.

The gel formed of norfloxacin does not settle out of solution like that formed with oxytetracycline but could have similar uses.

EXAMPLE 3

This Example illustrates the use of conazoles within the scope of the invention is making gels. The two conazoles used are miconazole and econazole. Both of these conazoles have side chains with two chlorinated benzene rings attached the imidazole ring, the difference being the number of chlorines on one of the benzene rings. The structures of miconazole (top) and econazole (bottom) are shown below.

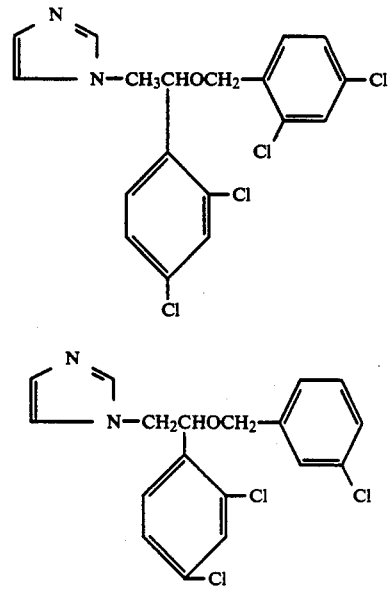

The procedure used to form each of the gels was identical. Table 3 has the materials used to form the miconazole gel.

TABLE 3

| | |
|---|---|
| Carboxymethylcellulose (CMC7HF) | 1 g |
| Water | 75 ml |
| Miconazole Nitrate | 1 g |
| Aluminum Acetate (boric salt) | 12.5 g |
| 0.9% Saline | 1.25 ml |
| Ethanol | 23.75 ml | while Table 4 has the materials used to form the econazole gel.

TABLE 4

| | |
|---|---|
| Carboxymethylcellulose (CMC7HF) | 1 g |
| Water | 75 ml |
| Econazole Nitrate | 1 g |
| Aluminum Acetate (boric salt) | 12.5 g |
| 0.9% Saline | 1.25 ml |
| Ethanol | 23.75 ml |

In both cases, 70 ml of water was heated to approximately 60° C. and the carboxymethylcellulose was dissolved therein to get a clear solution. The solution was cooled to room temperature and water was added to make a volume of 75 ml. At the same time, the aluminum acetate was dissolved into the 0.9% saline and mixed with 25 ml of the alcohol. The conazole was then dissolved into the aluminum acetate/saline/ethanol solution and the volume was raised to 25 ml with alcohol.

The two resulting solutions were then mixed together, e.g., using two syringes, to obtain even suspension. The material was allowed to gel for several hours at room temperature. The resulting gel became firmer with time. By changing the concentration of the ethanol (replacing it with water or saline), the properties of the gel can be modified.

In addition to the two conazoles described above, other conazoles without the aromatic side chains have been tried. None of these formed a gel, probably because they did not have a second site for a partial positive charge other than the ring structure. Accordingly, these other conazoles did not have the ability to ionically cross-link the carboxymethylcellulose properly.

The gels of the present invention could also have particulates, including lipid vesicles, suspended therein. Since these lipid vesicles can also be designed to carry a variety of materials which cannot otherwise be carried in the gel, a wound patch or other covering made of the gel with vesicles dispersed therein could be used to apply a variety of drugs on a sustained release basis to a selected site. Using this hybrid material, it would be possible to deliver incompatible materials by encapsulating one within a lipid vesicle and suspending the lipid vesicle within the gel containing the other.

Those skilled in the art will be able determine other modifications of the exemplary procedures and materials. Such other modifications are with the scope of the following claims.

What is claimed is:

1. A hydratable biodegradable gel consisting essentially of a callulosic compound with a DS of about 0.5 or greater cross-linked by an amount of an organic cross-linking agent selected from the group consisting of tetracylines, aromatic-substituted imidazoles, and quinolines, said cross-linking agent having at least two partial positive charge locations under conditions where said cellulosic compound has a localized negative charge, the amount of said cross-linking agent being sufficient to cross-link said cellulosic compound to form said gel.

2. The hydratable biodegradable gel of claim 1 wherein said tetracycline is selected from the group consisting of oxygetracycline and deoxytetracycline.

3. The hydratable biodegradable gel of claim 1 wherein said aromatic-substituted imidazole is conazole.

4. The hydratable biodegradable gel of claim 1 wherein said quinoline is norfloxacin.

5. A method of in vivo sustained release of an antibiotic in a body of an animal, comprising the steps of:

A. forming a hydratable biodegradable gel, by cross-linking a cullulosic compound with a DS of about 0.5 or greater with an amount of an antibiotic sufficient to cross-link said cellulosic compound and form said gel, said antibiotic selected from the group consisting of tetracylines, aromatic-substituted imidazoles, and quinolines, said antibiotic having at lesat two partial positive charge locations under conditions where said cellulosic compound has a localized negative charge;

B. delivering said gel to the body at a location where said sustained release is sought; and C. allowing said gel to dissociate, whereby said antibiotic is released in a sustained manner from said gel.

6. The method of claim 5 wherein said aromatic-substituted imidazole is a conazole.

7. The method of claim 5 wherein said tetracycline is selected from the group consisting of oxytetracycline and deoxytetracycline.

8. The method of claim 5 wherein the animal is a human.

9. The method of claim 5 wherein said quinoline is norfloxacin.

10. A hydratable biodegradable gel consisting essentially of a cellulosic compound with a high degree of carboxyl substitution cross-linked by an amount of an organic cross-linking agent selected from the group consisting of oxytetracycline, norfloxacin, miconazole, and econazole, said cross-linking agent having at least two partial positive charges under conditions where said cellulosic compound has a localized negative charge, the amount of said cross-linking agent being sufficient to cross-link said cellulosic compound to form said gel.

11. A hydratable biodegradable gel consisting essentially of a cellulosic compound with a high degree of carboxyl substitution cross-linked by an amount of an organic cross-linking agent selected from the group consisting of norfloxacin, miconazole, and econazole, said cross-linking agent having at least two partial positive charges under conditions where said cellulosic compound has a localized negative charge, the amount of said cross-linking agent being sufficient to cross-link said cellulosic compound to form said gel.

* * * * *